United States Patent [19]
Lois

[11] Patent Number: 5,944,688
[45] Date of Patent: Aug. 31, 1999

[54] IMPLANTABLE HEMODIALYSIS ACCESS PORT ASSEMBLY

[76] Inventor: William A Lois, 2233 E. 65th St., Brooklyn, N.Y. 11234

[21] Appl. No.: 09/119,247

[22] Filed: Jul. 20, 1998

[51] Int. Cl.[6] ..................................................... A61M 11/00
[52] U.S. Cl. .............................................. 604/93; 604/175
[58] Field of Search .................................. 604/93, 175, 4, 604/7, 8, 28–30, 43, 500, 523

[56] References Cited

U.S. PATENT DOCUMENTS

| | | | |
|---|---|---|---|
| 5,562,618 | 10/1996 | Cai et al. | 604/93 |
| 5,792,104 | 8/1998 | Speckman et al. | 604/175 X |
| 5,833,654 | 11/1998 | Powers et al. | 604/93 |

*Primary Examiner*—John D. Yasko
*Attorney, Agent, or Firm*—Michael I. Kroll

[57] ABSTRACT

An implantable dialysis access port assembly for connection of a dialysis machine to a patient and detoxifying blood within the patient. The implantable dialysis access port assembly includes a first port including a first device for receiving a first needle of the dialysis machine, and a first connector and a second port including a second devices for receiving a second needle of the dialysis machine, and a second connector. A first catheter is connected to extend from the first connector and into a vein of the patient and a second catheter is connected to extend from the second connector and into the vein of the patient. The first and second ports are of different geometrical shapes and are readily detectable in position below the skin of the patient such that when the first needle is received by the first receiving device, the second needle is received by the second receiving device and the dialysis machine is turned on, blood is caused to be removed from the vein through the first catheter, the first port and the first needle for detoxification in the dialysis machine and returned to the vein through the second needle, the second port and the second catheter.

20 Claims, 6 Drawing Sheets

IMPLANTABLE HEMODIALYSIS ACCESS PORT ASSEMBLY

BACKGROUND OF THE INVENTION

1. Field of the Invention The present invention relates generally to devices for providing access by a dialysis machine and, more specifically, to implantable hemodialysis ports which provide a cosmetically appealing dialysis adapter port for long term dialysis patients which are easily located and prevent the need for repeatedly performing surgery to relocate arteriovenous fistulas and external shunts due to scarring, vein damage and clotting.

2. Description of the Prior Art

Presently, two methods of performing dialysis on a patient are utilized. These methods are peritoneal dialysis and hemodialysis. Peritoneal dialysis is outside the scope of the present invention. In hemodialysis, blood is removed from the body and pumped through a machine. The blood is passed through a membrane in the machine which acts to remove any toxins from the blood prior to returning the blood to the patient. Hemodialysis is performed utilizing any of three possible surgical procedures.

A first of these surgical procedures involves forming an arteriovenous fistula between an artery and a vein, usually in the arm of the patient. The forming of the fistula causes the vein to enlarge thus making it ideal for the insertion of a catheter. With this method the vein must be repeatedly pierced. The repeated piercing of the vein causes scar tissue to develop and eventually leads to clotting within the fistula. When this occurs the surgery to insert a new fistula replacing the old fistula must be performed again.

Furthermore, as the kidney's of the patient are unable to remove waste, the veins are caused to become inflamed and thus it is difficult to find a suitable vein for insertion of the fistula.

A second surgical procedure involves using an externally extending shunt consisting of a tube for connecting and providing access to an implanted catheter. This procedure imposes a burden on the patient as the shunt extends outside of the body and is subject to infection. Furthermore, this procedure does not prevent clotting of the catheter and thus the patient may frequently need to have the catheter cleaned or replaced.

The third surgical procedure involves insertion of a totally implantable adapter device into the body of the patient. This procedure is an improvement over the previously discussed procedures as it prevents infection and provides a more durable platform for performing hemodialysis. However, this procedure is susceptible to clotting either due to the condition of the patient or oversight of the health care technician who fails to flush the catheter after each dialysis session.

Numerous types of dialysis access ports have been provided in the prior art. For example, U.S. Pat. Nos. 5,405,320; 5,480,380; 5,509,897 and 5,562,617 all are illustrative of such prior art. While these units may be suitable for the particular purpose to which they address, they would not be as suitable for the purposes of the present invention as heretofore described.

U.S. Pat. No. 5,405,320

Inventor: Zbylut J. Twardowski et al.

Issued: Apr. 11, 1995

A catheter for hemodialysis comprises a flexible catheter tube defining a plurality of separate lumens. The catheter defines an arc angle of generally U-shape in its natural, unstressed configuration. Thus, the catheter may be implanted with a distal catheter portion residing in a vein of the patient, the distal catheter portion being of substantially the shape of the vein in its natural, unstressed condition. Also, a proximal catheter portion resides in a surgically created tunnel extending from the vein and through the skin of the patient, this section of the catheter also being typically in its natural, unstressed condition. Thus blood may be removed from the vein through one lumen of the catheter, and blood may be returned to the vein through another lumen of the catheter, while the catheter is subject to long term indwelling in the body. Improved results are achieved because of the lack of mechanical stress in the shape of the catheter, which stress causes the catheter to press unduly against adjacent tissues.

U.S. Pat. No. 5,480,380

Inventor: Geoffrey S. Martin

Issued: Jan. 2, 1996

The invention provides a dual lumen catheter comprising outer and inner tube materials. A main portion extends axially and has a selected first cross-section. The main portion includes main portions of the respective outer and inner tube materials which together define an annular intake lumen and a main portion of a return lumen contained inside the intake lumen. A tubular transition portion is made up integrally of both the outer and inner tube materials and has a second cross-section smaller than the first cross-section. The transition portion extends axially from the distal end of the main portion and this can be extended to include a tip portion made up only of outer tube material and which extends axially from the transition portion. The transition portion on its own, or with the tip portion, defines a tip section which is a continuation of said main part of the return lumen to complete the return lumen.

U.S. Pat. No. 5,509,897

Inventor: Zbylut J. Twardowski et al.

Issued: Apr. 23, 1996

A catheter for hemodialysis comprises a flexible catheter tube defining a plurality of separate lumens. The catheter defines an arc angle of generally U-shape in its natural, unstressed configuration. Thus, the catheter may be implanted with a distal catheter portion residing in a vein of the patient, the distal catheter portion being of substantially the shape of the vein in its natural, unstressed condition. Also, a proximal catheter portion resides in a surgically created tunnel extending from the vein and through the skin of the patient, this section of the catheter also being typically in its natural, unstressed condition. Thus blood may be removed from the vein through one lumen of the catheter, and blood may be returned to the vein through another lumen of the catheter, while the catheter is subject to long term indwelling in the body. Improved results are achieved because of the lack of mechanical stress in the shape of the catheter, which stress causes the catheter to press unduly against adjacent tissues.

U.S. Pat. No. 5,562,617

Inventor: Charles D. Finch Jr. et al.

Issued: Oct. 8, 1996

An implantable device grafted directly to vascular structures for high volume blood and/or fluid infusion and/or removal for such purpose as hemodialysis, apheresis, exchange transfusion, or large volume fluid infusion. The device is also adaptable to intermittent access to the venous or arterial circulation for purpose of blood sampling or giving medications. The device is comprised of an implantable fluid chamber connected to a vascular shunt which is then grafted directly to the vascular structure (e.g. artery or vein). The vascular end of the device employs a valve to prevent reflux of blood and subsequent washout of anticoagulant during periods when the device is not in use. The device is accessed percutaneously with a needle or needle-introduced catheter and is filled with anticoagulant prior to needle withdrawal to prevent thrombosis.

SUMMARY OF THE PRESENT INVENTION

The present invention relates generally to adapters for connection with a dialysis machine and, more specifically, to implantable hemodialysis ports which provide a cosmetically appealing dialysis adapter port for long term dialysis patients are easily located and prevent the need for repeatedly performing surgery to relocate arteriovenous fistulas and external shunts due to scarring, vein damage and clotting.

A primary object of the present invention is to provide an implantable dialysis port assembly that will overcome the shortcomings of prior art devices.

Another object of the present invention is to provide an implantable dialysis port assembly which is able to provide a cosmetically pleasing and easily accessible port for insertion of the needles extending from the terminals of a dialysis machine.

A further object of the present invention is to provide an implantable dialysis port assembly which is able to provide a patient with a normal lifestyle between dialysis treatments by removing any risk of infection associated with externally extending dialysis ports.

A yet further object of the present invention is to provide an implantable dialysis port assembly wherein the port includes first and second subcutaneously located terminals, each for receiving first and second needles connected to the terminals of the dialysis machine.

A still further object of the present invention is to provide an implantable dialysis port assembly wherein the first and second subcutaneously located terminals differ in shape and are easily detected through the application of light pressure to the skin.

A further object of the present invention is to provide an implantable dialysis port assembly wherein the first and second subcutaneously located terminals have an enlarged surface providing a large number of possible needle insertion points and thereby allowing the insertion area to heal prior to reinsertion during a subsequent dialysis treatment.

A further object of the present invention is to provide an implantable dialysis port assembly wherein the first and second subcutaneously located terminals are formed from a self sealing material able to prevent the release of any fluids therethrough.

Another object of the present invention is to provide an implantable dialysis port assembly wherein the first and second subcutaneously located terminals are lined with a material able to prevent piercing of the terminal wall by the needle.

Another object of the present invention is to provide an implantable dialysis port assembly that is simple and easy to use.

A still further object of the present invention is to provide an implantable dialysis port assembly that is economical in cost to manufacture.

Additional objects of the present invention will appear as the description proceeds.

An implantable dialysis access port assembly for connection of a dialysis machine to a patient and detoxifying blood within the patient is disclosed by the present invention. The implantable dialysis access port assembly includes a first port including a first device for receiving a first needle of the dialysis machine, and a first connector and a second port including a second devices for receiving a second needle of the dialysis machine, and a second connector. A first catheter is connected to extend from the first connector and into a vein of the patient and a second catheter is connected to extend from the second connector and into the vein of the patient. The first and second ports are of different geometrical shapes and are readily detectable in position below the skin of the patient such that when the first needle is received by the first receiving device, the second needle is received by the second receiving device and the dialysis machine is turned on, blood is caused to be removed from the vein through the first catheter, the first port and the first needle for detoxification in the dialysis machine and returned to the vein through the second needle, the second port and the second catheter.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

Figure 2:
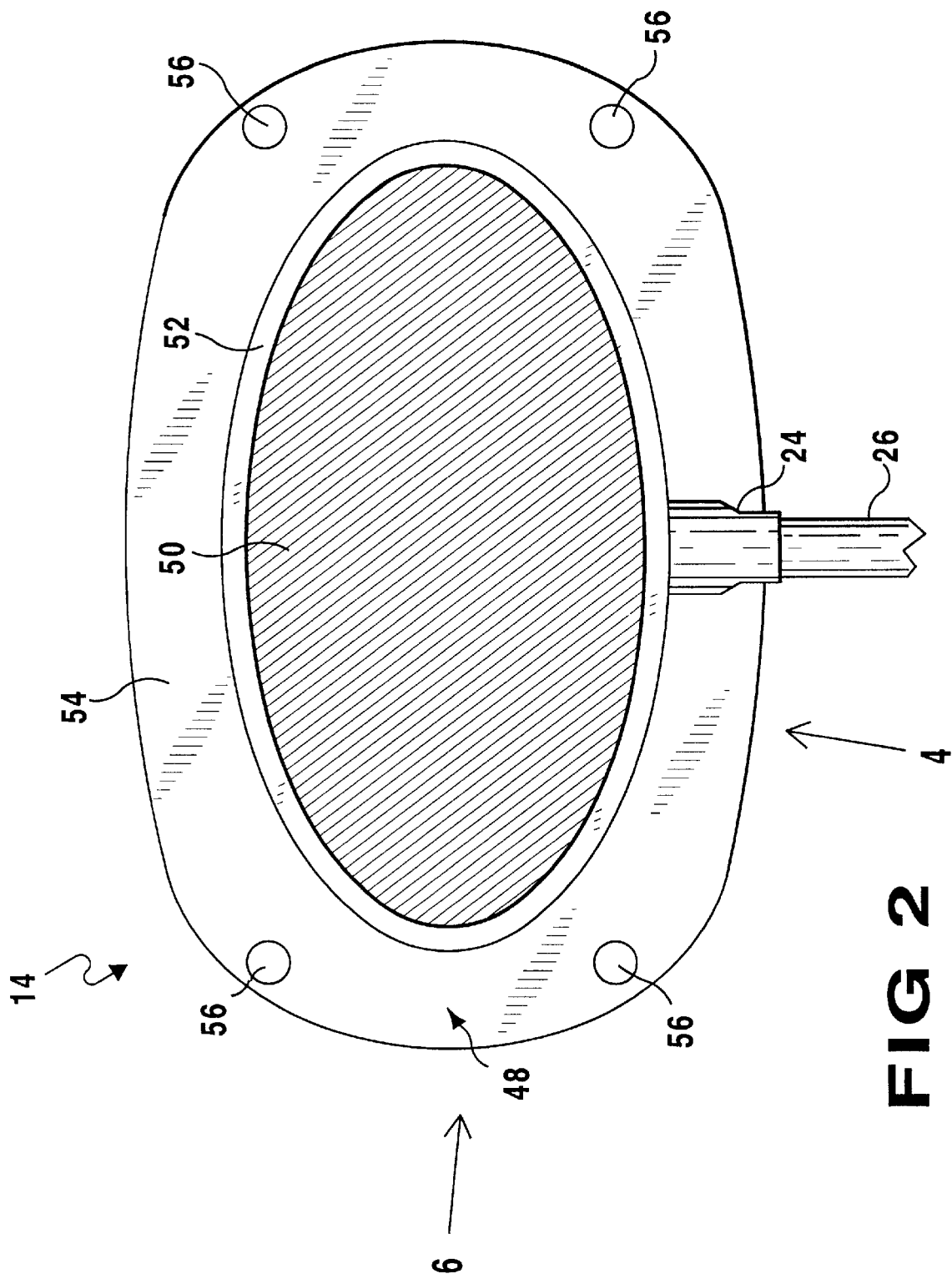
FIG. 2 is a top view of the venous port of the implantable dialysis access port assembly of the present invention taken in the direction of the arrow labeled 2 of FIG. 1.
Figure 3:
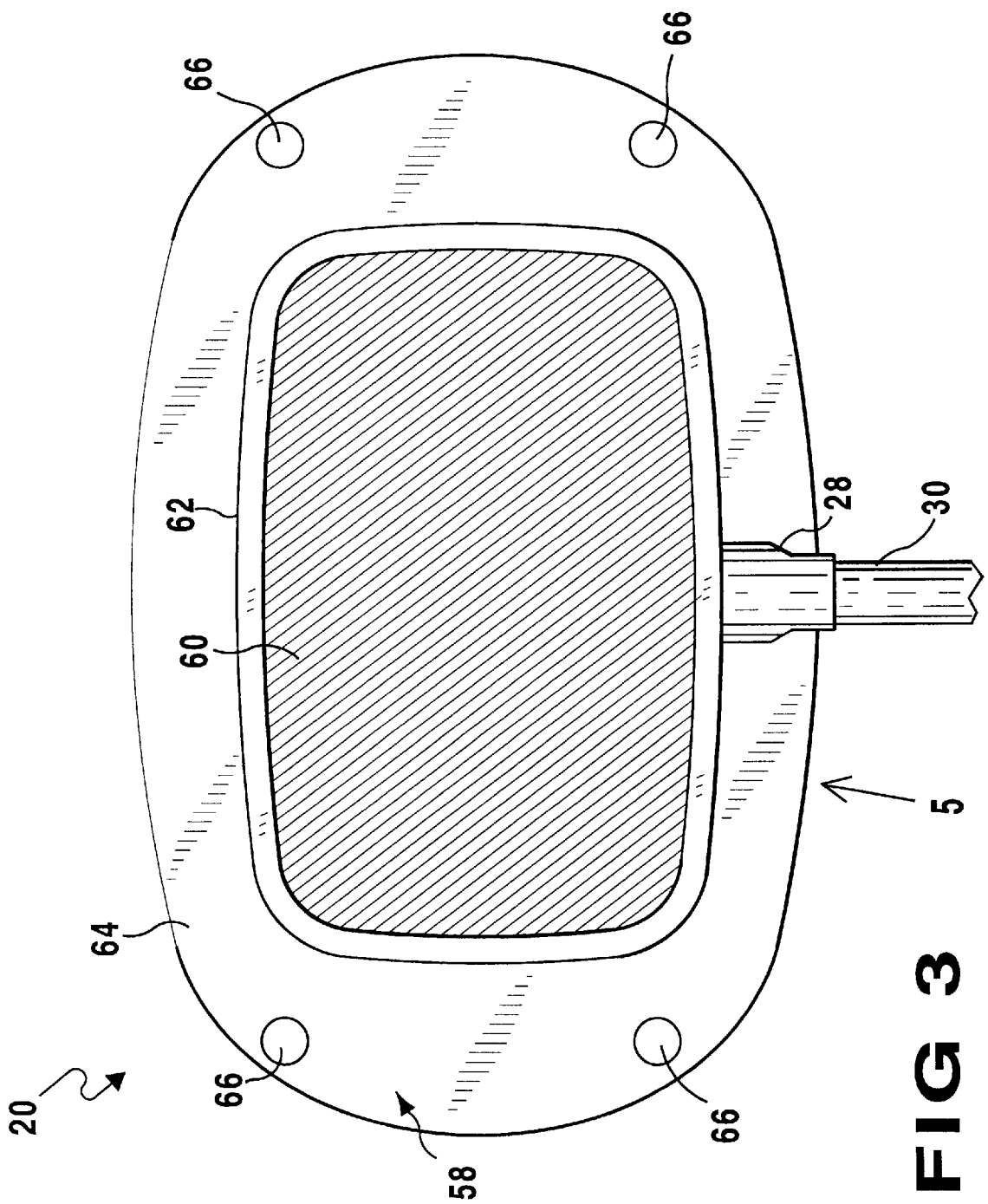
FIG. 3 is a top view of the arterial port of the implantable dialysis access port assembly of the present invention taken in the direction of the arrow labeled 3 of FIG. 1.
Figure 5:
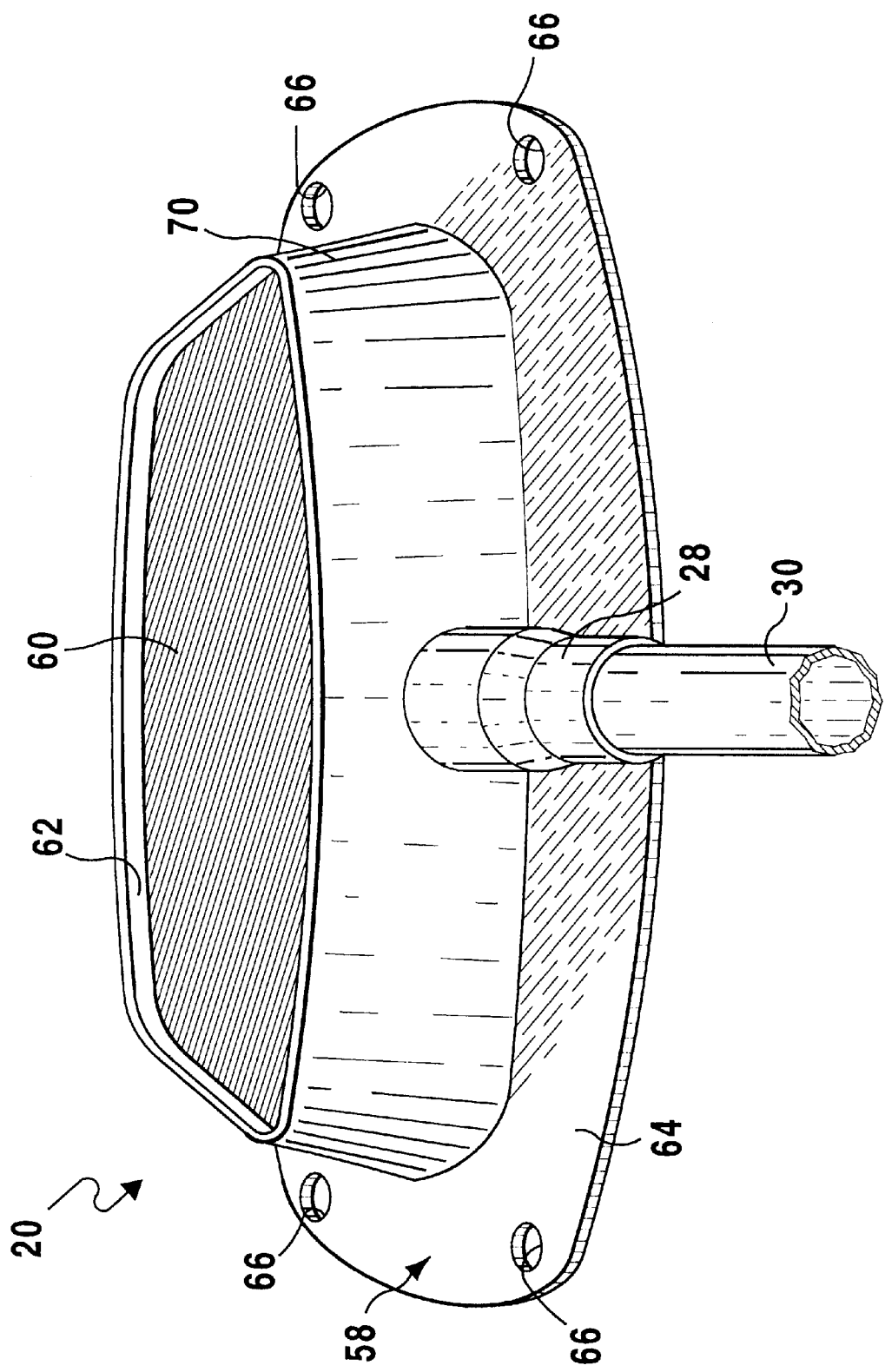
Figure 6:
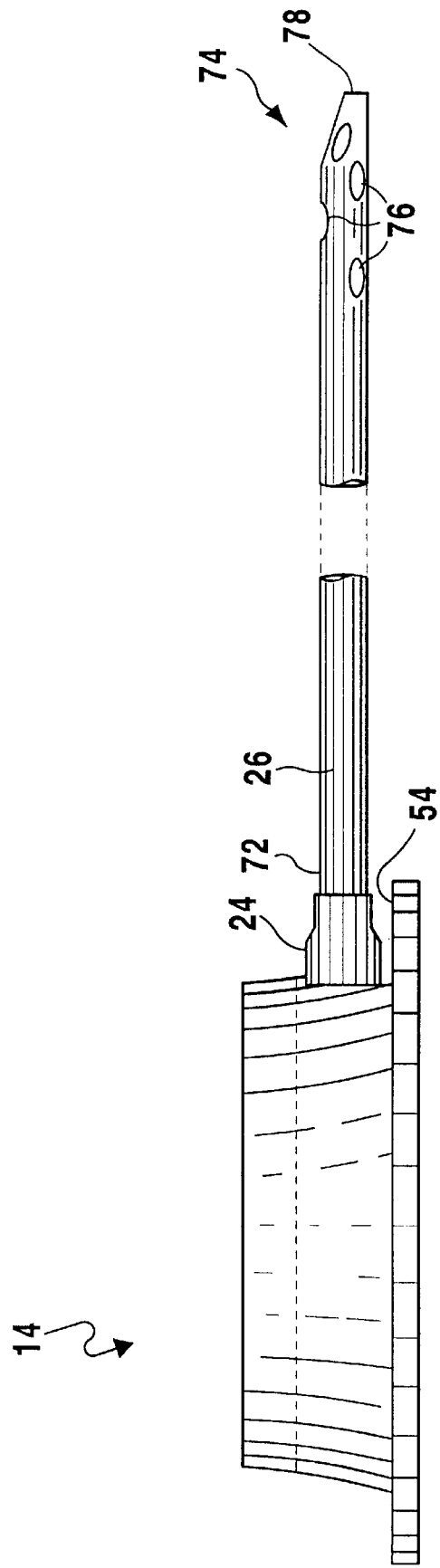

FIG. 5 is a side perspective view of the arterial port of the implantable dialysis access port assembly of the present invention taken in the direction of the arrow labeled 5 of FIG. 3 showing the septum with the catheter broken away; and FIG. 6 is a side view of the venous port of the implantable dialysis access port assembly of the present invention taken in the direction of the arrow labeled 6 of FIG. 2 showing the catheter and tapered catheter tip extending therefrom.

DESCRIPTION OF THE REFERENCED NUMERALS

Turning now descriptively to the drawings, in which similar reference characters denote similar elements throughout the several views, the Figures illustrate the implantable dialysis access port assembly of the present invention. With regard to the reference numerals used, the following numbering is used throughout the various drawing figures.

10 implantable dialysis access port assembly of the present invention
12 patient
14 first port
16 first needle
18 dialysis machine
20 second port
22 second needle
24 first passageway
26 first catheter
28 second passageway
30 second catheter
32 vein
34 heart
36 arrows indicating direction of blood flow through the second port
38 arrows indicating direction of blood flow through the first port
40 first tube
42 second tube
44 pump of dialysis machine
46 membrane of dialysis machine
48 face side of first port
50 first enlarged area
52 lining material of first port
54 boarder area of first port
56 recess extending through boarder area of first port
58 face side of second port
60 second enlarged area
62 lining material of second port
64 boarder area of second port
66 recess extending through boarder area of second port
68 side wall of first port
70 side wall of second port
72 first end of catheter
74 second end of catheter
76 recesses extending about and through second end of catheter
78 exit port in second end of catheter

DETAILED DESCRIPTION OF THE PREFERRED EMBODIMENT

Turning now descriptively to the drawings, in which similar reference characters denote similar elements throughout the several views, FIGS. 1 through 6 illustrate the implantable dialysis access port assembly of the present invention indicated generally by the numeral 10.

Figure 1:
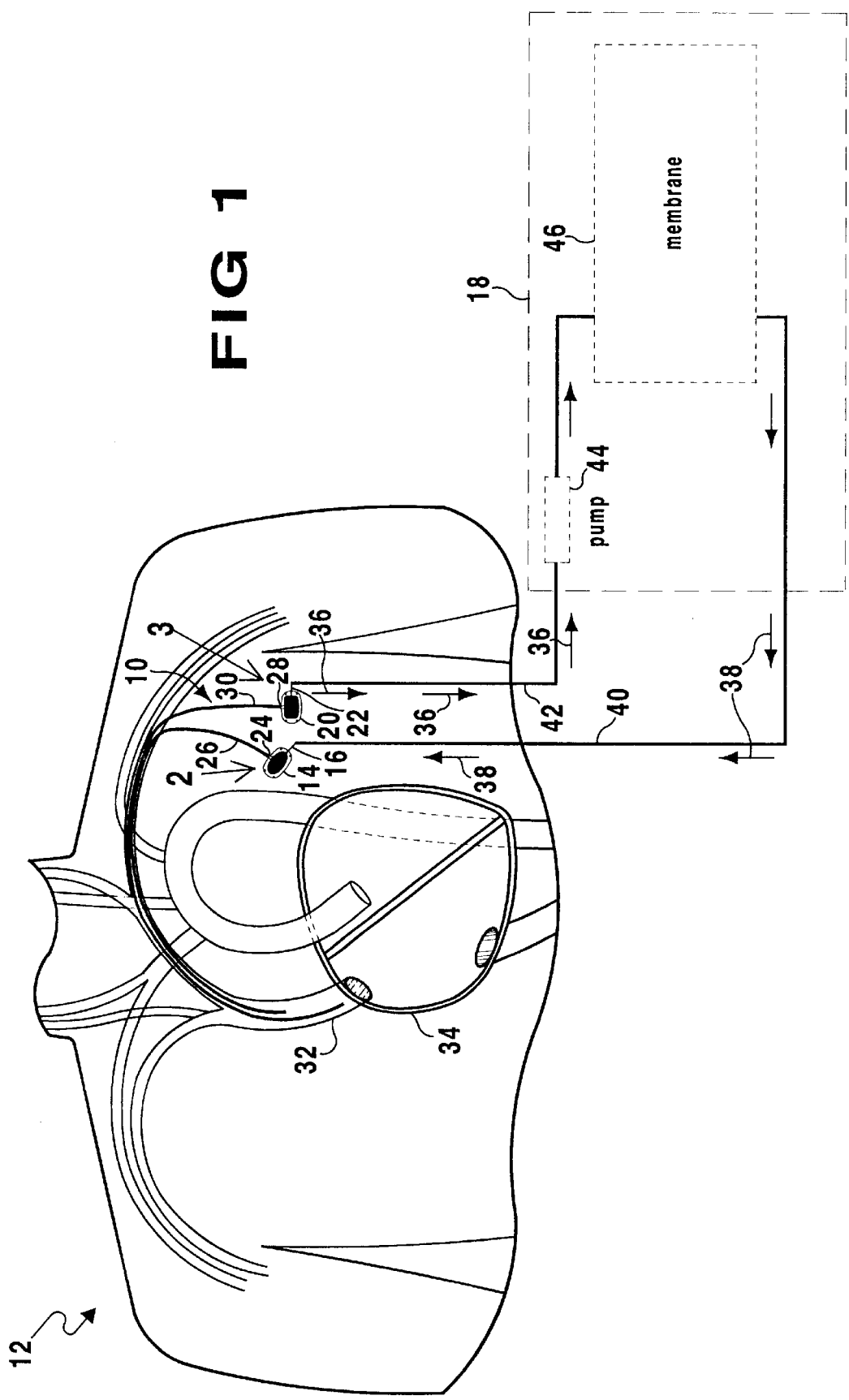
FIG. 1 is a perspective view of the internal organs of a patient in which the implantable dialysis access port assembly of the present invention is inserted and connected for hemodialysis treatment.

The implantable dialysis access port assembly 10 is illustrated in FIG. 1 positioned below subcutaneous tissue in a left subclavicular area of a patient 12. The implantable dialysis access port assembly 10 includes a first venous port 14 for receiving a first needle 16 from a dialysis machine 18 and a second arterial port 20 for receiving a second needle 22 from the dialysis machine 18.

Extending from the first venous port 14 is a first passageway 24 for connection to a first catheter 26. A second passageway 28 extends from the second arterial port 20 for connection with a second catheter 30. The first and second catheters 26 and 30, respectively, are both positioned in a vein 32 supplying blood to the heart 34. Preferably, the first and second catheters 26 and 30, respectively, are positioned to extend into the superior vena cava of the patient 12. The superior vena cava supplies oxygen depleted blood from the upper extremities to the heart 34. The second catheter 30 is positioned to extend further into the vein 32 and closer to the heart 34 than the first catheter 26 and acts to remove blood from the vein 32 as is shown by the arrows labeled 36 in FIG. 1. The blood removed from the vein 32 is supplied to the dialysis machine 18 connected to the second port 20 for detoxification. The first catheter 26 extends into the vein 32 a distance less than the second catheter 30 and acts to return the detoxified blood from the dialysis machine 18 to the vein 32 as shown by the arrows labeled 38 in FIG. 1. The blood is returned through the first port 14 and first catheter 26 into the vein 32 for supplying the detoxified blood to the heart 34 for pumping around the body of the patient 12.

A first tube 40 extends between the first needle 16 and the dialysis machine 18 and a second tube 42 extends between the second needle 22 and the dialysis machine 18. The second tube 42 is connected to a pump 40 within the dialysis machine 18 which acts to draw the blood from within the vein 32 through the second tube 42. The second tube 42 delivers the blood to a membrane 46 within the dialysis machine 18. The membrane 46 acts to remove the toxins contained within the blood and provides the blood passing therethrough back to the first port 14 and eventually to the vein 32 through the first tube 40.

FIG. 2 illustrates an enlarged view of the first port 14 of the implantable dialysis access port assembly 10. From this view a face side 48 of the first port 14 is clearly seen. Positioned on the face side 48 is a first enlarged area 50 formed of a self sealing material for receiving the first needle 16. The enlarged size of the first area 50 provides for numerous amounts of insertion points at which the first needle 16 may extend through thereby allowing an area through which the first needle 16 has been inserted time to heal prior to additional needle insertions. The self sealing material is preferably formed of rubberized silicone. However, any other suitable material which is able to reseal a hole formed by insertion of the first needle 16 and thereby prevent the release of any fluids passing therethrough except via the first needle 16 may be used. The first enlarged area 50 is also of a distinctive shape whereby it can be readily discovered upon application of light pressure to the patient's skin. FIG. 2 illustrates the first area 50 in the shape of an oval. The shape of the first area as an oval is for purposes of illustration only and not meant to limit the present invention in any manner. The first enlarged area 50 is further lined with a material 52 having a density able to prevent the needle from piercing the defining walls thereof. The dense material is preferably titanium although any material able to prevent the needle from passing therethrough may be used.

The first port 14 further includes a boarder area 54 extending therearound with a plurality of recesses 56 extending through the boarder area 54. The first port 14 of the implantable dialysis access port assembly 10 is secured in position by suchering the boarder area 54 through the plurality of recesses 56 and thereby is prevented from moving. Extending from the enlarged area 50 is the first passageway 24. The first passageway 24 connects the first catheter 26 to the first enlarged area 50 thereby providing a conduit for the blood to flow from the needle through the first catheter 26 and back to the vein 32.

FIG. 3 illustrates an enlarged view of the second port 20 of the implantable dialysis access port assembly 10. From this view a face side 58 of the second port 20 is clearly seen. Positioned on the face side 58 is a second enlarged area 60 formed of a self sealing material for receiving the second needle 22. The enlarged size of the second area 60 provides for numerous amounts of insertion points at which the second needle 22 may extend through thereby allowing an area through which the second needle 22 has been inserted time to heal prior to additional needle insertions. The self sealing material is preferably formed of rubberized silicone. However, any other suitable material which is able to reseal a hole formed by insertion of the second needle 22 and thereby prevent the release of any fluids passing therethrough except via the second needle 22 may be used. The second enlarged area 60 is also of a distinctive shape whereby it can be readily discovered upon application of light pressure to the patient's skin. FIG. 3 illustrates the second area 60 in the shape of a rectangle. The shape of the second area 60 as a rectangle is for purposes of illustration only and not meant to limit the present invention in any manner. The only limitation on the shape of the second enlarged area 60 is that is must be of a different shape than the first enlarged area 50 thereby allowing the first and second enlarged areas to be readily distinguishable from one another. The second enlarged area 60 is further lined with a material 62 having a density able to prevent the needle from piercing the defining walls thereof. The dense material is preferably titanium although any material able to prevent the needle from passing therethrough may be used.

The second port 20 further includes a boarder area 64 extending therearound with a plurality of recesses 66 extending therethrough. The second port 20 of the implantable dialysis access port assembly 10 is secured in position by suchering the boarder area 64 through the plurality of recesses 66 and thereby preventing the second port 20 from moving. Extending from the enlarged area 60 is the second passageway 28. The second passageway 28 connects the second catheter 30 to the second enlarged area 60 thereby providing a conduit for the blood to flow from the vein 32 through the first catheter 30 and to the second needle 22 for detoxification in the dialysis machine 18.

Figure 4:
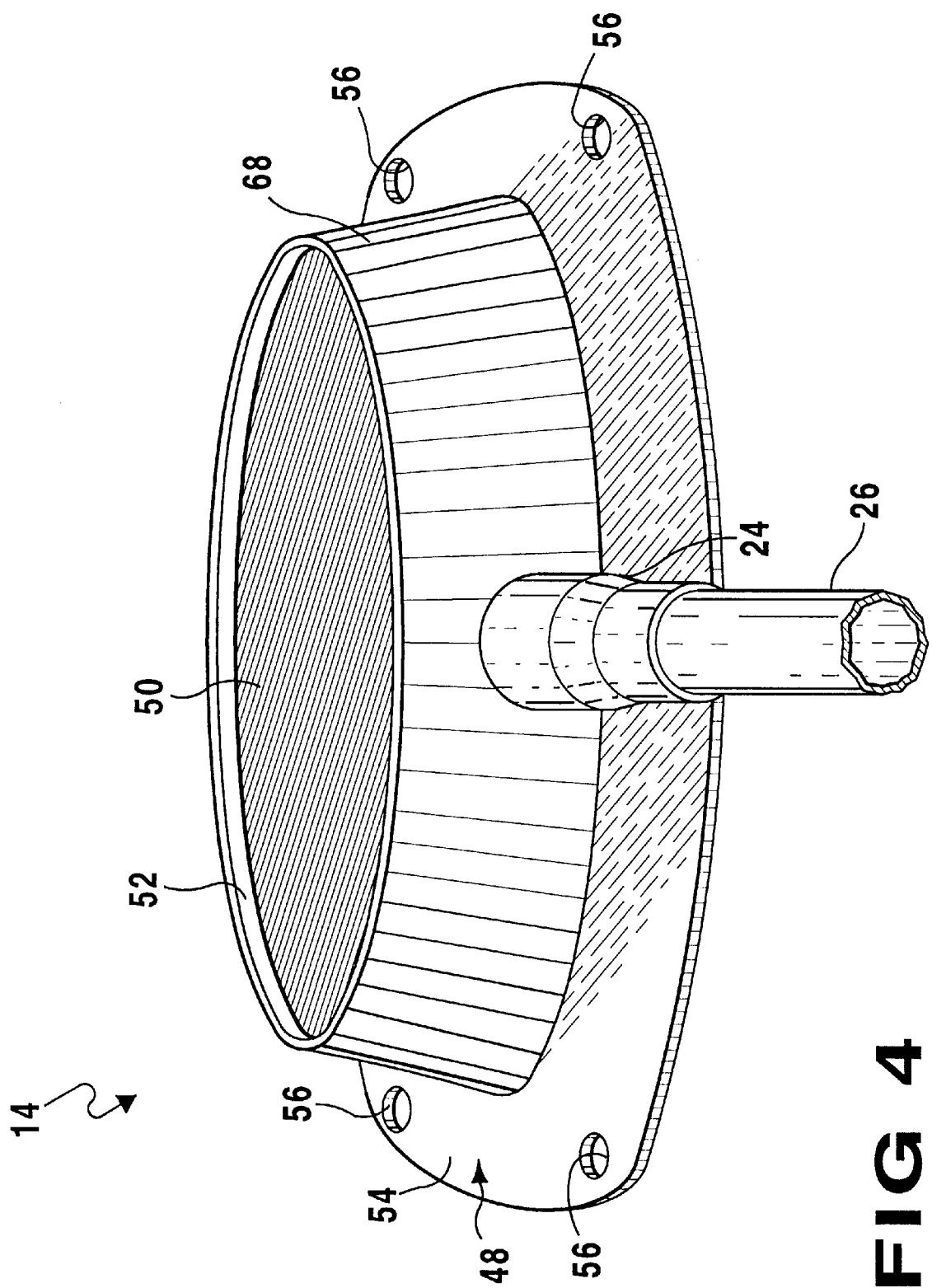
FIG. 4 is a side perspective view of the venous port of the implantable dialysis access port assembly of the present invention taken in the direction of the arrow labeled 4 of FIG. 2 showing the septum with the catheter broken away.

FIG. 4 illustrates a side view of the first port 14. As can be seen from this view, the first port 14 further includes a side wall 68 extending from the boarder area 54. The side wall 68 forms a pool in which the first enlarged area 50 sits. The side wall 68 is lined with the dense material preventing the first needle 16 from piercing the side wall 68 and passing therethrough. The first enlarged area 50 is preferably of a thickness or height less than the height of the side wall 68 allowing a reservoir to form therebelow. The first passageway 24 is positioned to extend into the reservoir and when the first needle 16 extends through the first enlarged area 50 it extends into the reservoir. This allows the blood flowing through the first needle 16 to be deposited in the reservoir for delivery through the first passageway 24 to the first catheter 26 and back to the vein 32.

FIG. 5 illustrates a side view of the second port 20. As can be seen from this view, the second port 20 further includes a side wall 70 extending from the boarder area 64. The side wall 70 forms a pool in which the second enlarged area 60 sits. The side wall 70 is lined with the dense material preventing the second needle 22 from piercing the side wall 70 and passing therethrough. The second enlarged area 60 is preferably of a thickness or height less than the height of the side wall 70 allowing a reservoir to form therebelow. The second passageway 28 is positioned to extend into the reservoir and when the second needle 22 extends through the second enlarged area 60 it extends into the reservoir. This allows the blood flowing from the vein 32 through the second catheter 30 and second passageway 28 to be deposited in the reservoir for delivery through the second needle 22 to the second tube 36 and to the dialysis machine 18.

FIG. 6 illustrates a side view of the first port 14 and first catheter 26. From this view it can be seen that the first catheter 26 is connected at a first end 72 to the first passageway 24 and extends therefrom. At a second end 74 of the first catheter 26 opposite the first end 72 are a plurality of recesses 76 positioned therearound and extending therethrough. The first catheter 26 is hollow thereby allowing liquids such as blood to flow therethrough. Furthermore, at the second end 74 of the first catheter 26 is an exit port 78 allowing liquid to pass therethrough or thereout depending upon the function of the catheter. The second catheter 30 is similar in construction to the first catheter 26 and it is therefore not necessary to describe the second catheter 30. The only difference between the first and second catheters 26 and 30, respectively, is the length of each.

The operation of the implantable dialysis access port assembly 10 will now be described with reference to the figures. In operation, the implantable dialysis access port 10 is prepared for implantation below subcutaneous tissue in a left subclavicular area of a patient 12. The first and second ports 14 and 20, respectively, are connected to the first and second catheters 26 and 30 at the first and second connection ports 24 and 26, respectively. When the implantable dialysis access port assembly 10 is implanted in the body of the patient, the first and second catheters 26 and 30 are positioned to extend into a vein, preferably the superior vena cava, of the patient 12 and the first and second ports 14 and 20 are suchered through the recesses 56 and 66 in their respective boarder areas 54 and 64 to the subcutaneous tissue in the left subclavicular area of the patient 12. The second catheter 30 is preferably inserted deeper into the vein and closer to the heart 34 than the first catheter 26. The implantable dialysis access port assembly 10 is now secured within the body of the patient 12 and ready for use. The implantable dialysis access port assembly 10 may be located by simply feeling around the area of implantation until located. The presence of the implantable dialysis access port assembly 10 is easily detectable as the first and second ports 14 and 20 are positioned slightly below the surface of the skin and can be detected by applying light pressure to the skin of the patient 12. The first and second ports 14 and 20 are each of a particular shape and thus can be easily differentiated from one another.

When ready for use, the doctor will feel around the area of implantation to locate the first and second ports 14.and 20, respectively. Upon finding the first port 14, the first needle 16 connected to the first tube 40 from the dialysis machine 18 is inserted into the first enlarged area 50 such that the first needle 16 extends through the first enlarged area 50 and into the reservoir formed therebelow. When the second port 20 is located, the second needle 22 connected to the second tube 42 from the dialysis machine 18 is inserted therein such that the second needle 22 extends through the second enlarged area 60 and into the reservoir formed therebelow. The second port 20 is connected to the pump 44 whereby blood is drained from the vein 32 through the second catheter 30. The first port is connected to the output side of the membrane 44 within the dialysis machine 18 via the first needle 16 and the first tube 40 and thus blood is delivered back to the vein 32 therethrough.

Once the needles are inserted into their respective ports the patient 12 is prepared to begin dialysis treatment. When the dialysis machine 18 is turned on, blood is drawn through the second catheter 30 into the reservoir in the second port 20 by a suction force exerted through the second needle 22 and second tube 42 by the pump 44. The blood flows through the second needle 22 and the second tube 42 into the dialysis machine 18. In the dialysis machine 18, the blood is passed through the membrane 46 which acts to detoxify the blood. The blood is then returned through the first tube 40 and first needle to the reservoir in the first port 14. The blood in the reservoir is then passed through the first passageway 24 and first catheter 28 back into the vein 32.

Once the blood of the patient 12 is detoxified, the dialysis machine 18 is turned off and the first and second needles 16 and 22, respectively, are removed from their respective enlarged areas. As the first and second enlarged areas 50 and 60 are formed of a sealable rubberized silicone material, the hole formed by the insertion of the needle is resealed once the needle is removed and thus the port is prepared for reuse. This also allows the port to be used a substantial number of times without the need for replacement thus increasing the life of the implantable dialysis access port assembly 10.

From the above description it can be seen that the implantable dialysis access port assembly of the present invention is able to overcome the shortcomings of prior art devices by providing a implantable dialysis access port assembly which is cosmetically pleasing and provides an easily accessible port for insertion of the needles extending from the terminals of a dialysis machine while allowing a patient to maintain a normal lifestyle between dialysis treatments by removing any risk of infection associated with externally extending dialysis ports. The implantable dialysis port assembly includes first and second subcutaneously located terminals, each for receiving first and second needles connected to the terminals of the dialysis machine which differ in shape, are easily detected through the application of light pressure to the skin and have an enlarged surface providing a large number of possible needle insertion points and thereby allowing the insertion area to heal prior to reinsertion during a subsequent dialysis treatment. The first and second subcutaneously located terminals are formed from a self sealing material able to prevent the release of any fluids therethrough and are lined with a material able to prevent piercing of the terminal wall by the needle. Furthermore, the implantable dialysis access port assembly of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An implantable dialysis access port assembly for connection of a dialysis machine to a patient and detoxifying blood within the patient, said implantable dialysis access port assembly comprising:
    a) a first port including a first means for receiving a first needle of the dialysis machine, and a first connector;
    b) a second port including a second means for receiving a second needle of the dialysis machine, and a second connector;
    c) a first catheter connected to extend from said first connector and into a vein of the patient;
    d) a second catheter connected to extend from said second connector and into the vein of the patient, wherein said first and second ports are of different geometrical shapes and are readily detectable in position below the skin of the patient such that when the first needle is received by said first receiving means, the second needle is received by said second receiving means and the dialysis machine is turned on, blood is caused to be removed from the vein through said first catheter, said first port and the first needle for detoxification in the dialysis machine and returned to the vein through the second needle, said second port and said second catheter.

2. The implantable dialysis access port assembly as recited in claim 1, wherein said assembly is implanted in a position below subcutaneous tissue in a left subclavicular area of the patient's body.

3. The implantable dialysis access port assembly as recited in claim 1, wherein the first and second needles each include a first and second tube extending therefrom for providing the blood removed from the vein through said first catheter and first port to the dialysis machine and returning the blood from the dialysis machine to the vein through said second port and second catheter.

4. The implantable dialysis access port assembly as recited in claim 3, wherein said first and second enlarged areas each have a thickness and said first and second ports each include a side wall extending therefrom and forming a reservoir therein for receiving said first and second receiving means, said side walls each having a height greater than the thickness of the first and second receiving means.

5. The implantable dialysis access port assembly as recited in claim 4, wherein said reservoir in both said first and second ports includes a base side, said base side in said reservoir of said first port being separated from said first receiving means received thereby forming a first pool therebetween and said base side in said reservoir of said second port being separated from said second receiving means forming a second pool therebetween.

6. The implantable dialysis access port assembly as recited in claim 5, wherein said first and second receiving means are both formed of a self sealing material.

7. The implantable dialysis access port assembly as recited in claim 6, wherein said self sealing material is rubberized silicone.

8. The implantable dialysis access port assembly as recited in claim 7, wherein said first and second side walls are each coated with a material able to prevent the first and second needles from piercing said respective side wall upon being received by said first and second receiving means.

9. The implantable dialysis access port assembly as recited in claim 8, wherein the first needle extends from the first tube and through said first receiving means into said first pool and the second needle extending from the second tube extends through said second receiving means and into said second pool.

10. The implantable dialysis access port assembly as recited in claim 1, wherein said first port further includes first means for securing said first port within the body of the patient and said second port further includes second means for securing said first port within the body of the patient.

11. The implantable dialysis access port assembly as recited in claim 2, wherein said first port further includes first means for securing said first port within the body of the patient and said second port further includes second means for securing said second port within the body of the patient.

12. The implantable dialysis access port assembly in claim 10, wherein said first and second means for securing each include a boarder area extending around a periphery of said respective one of said first and second ports and at least one recess extending through said border area.

13. The implantable dialysis access port assembly in claim 11, wherein said first and second means for securing each include a boarder area extending around a periphery of said respective one of said first and second ports and at least one recess extending through said border area.

14. The implantable dialysis access port assembly in claim 12, wherein said first and second ports are secured within the body of the patient by suchering each of said means for securing thereto.

15. The implantable dialysis access port assembly in claim 13, wherein said first and second ports are secured within the body of the patient by suchering each of said means for securing thereto.

16. The implantable dialysis connection assembly as recited in claim 1, wherein said first and second receiving means each have a surface area of a size able to provide a large number of insertion points thereby allowing an area time to heal after puncture with a needle.

17. The implantable dialysis access port assembly in claim 1, wherein said first port has an oval shape and said second port has a rectangular shape.

18. The implantable dialysis access port assembly in claim 1, wherein said first port has a rectangular shape and said second port has an oval shape.

19. The implantable dialysis access port assembly in claim 1, wherein said first and second catheters each have a length, the length of said first catheter being greater than the length of said second catheter.

20. The implantable dialysis access port assembly in claim 1, wherein said first catheter is inserted deeper into the vein than said second catheter.

* * * * *